United States Patent
Brown (10) Patent No.: US 11,238,625 B2
(45) Date of Patent: Feb. 1, 2022

(54) IMAGING SYSTEM EXTENDED FIELD-OF-VIEW

(71) Applicant: KONINKLIJKE PHILIPS N.V., Eindhoven (NL)

(72) Inventor: Kevin Martin Brown, Chardon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 19 days.

(21) Appl. No.: 16/637,947

(22) PCT Filed: Aug. 8, 2018

(86) PCT No.: PCT/EP2018/071440
§ 371 (c)(1),
(2) Date: Feb. 10, 2020

(87) PCT Pub. No.: WO2019/034486
PCT Pub. Date: Feb. 21, 2019

(65) Prior Publication Data
US 2020/0175730 A1    Jun. 4, 2020

Related U.S. Application Data (60) Provisional application No. 62/545,520, filed on Aug. 15, 2017.

(51) Int. Cl.
*G06T 11/00* (2006.01)
*A61B 6/03* (2006.01)

(52) U.S. Cl.
CPC ............ *G06T 11/003* (2013.01); *A61B 6/035* (2013.01); *G06T 2211/432* (2013.01)

(58) Field of Classification Search
CPC ...... G06T 11/00; G06T 11/003; G06T 11/005; G06T 2211/432; A61B 6/00; A61B 6/03; A61B 6/035
See application file for complete search history.

(56) References Cited

U.S. PATENT DOCUMENTS

| 7,515,676 B2 | 4/2009 | Zamyatin |
| 2007/0253523 A1 | 11/2007 | Zamyatin |

FOREIGN PATENT DOCUMENTS

| CN | 104751502 A | 7/2015 |
| CN | 105761226 A | 7/2016 |

OTHER PUBLICATIONS

PCT International Search Report, International application No. PCT/EP2018/071440, dated Nov. 12, 2018.
(Continued)

*Primary Examiner* — Jurie Yun
(74) *Attorney, Agent, or Firm* — Larry Liberchuk (57) ABSTRACT

An imaging system includes a rotating gantry with a bore, and an X-ray radiation source supported by the rotating gantry, which rotates around the bore and emit X-ray radiation that traverses at least a portion of the bore. A detector array supported by the rotating gantry, located opposite the X-ray radiation source, detects the X-ray radiation having traversed an object located within the bore and generate projection data indicative of the detected X-ray radiation, wherein the projection data comprises a sinogram. A processor estimates a portion of the object truncated in the sinogram by fitting a curve to data sampled from a plurality of views of the object in the sinogram adjacent to a set of truncated views of the object in the sinogram, and reconstructs an image of the object based on the estimated portion of the object truncated and the generated projection data.

14 Claims, 6 Drawing Sheets

(56) References Cited

OTHER PUBLICATIONS

Zamyatin Alexander et al: "Extension of the Reconstruction Field of View and Truncation Correction Using Sinogram Decomposition", Medical Physics, AIP, Melville, NY, US, vol. 34, No. 5, Apr. 18, 2007 (Apr. 18, 2007), pp. 1593-1604, XP012103397.
Hsieh S.S. et al., "An Algorithm to Estimate the Object Support in Truncated Images", Medical Physics, vol. 41, No. 7, Jul. 2014, pp. 071908-071911.
Hsieh J. et al., "A Novel Reconstruction Algorithm to Extend the CT Scan Field-of-View", Medical Physics, 31 (9), Sep. 2004, pp. 2385-2391.
Chityala R. et al., "Artifact Reduction in Truncated CT Using Sinogram Completion", Proc SPIE Int Soc Opt Eng. Feb. 2005 ; 5747(3): 2110-2117.
Li B. et al., "An Enhanced Reconstruction Algorithm to Extend CT Scan Field-of-View with Z-Axis Consistency Constraint", Med Phys. Oct. 2012;39(10):6028-34.

IMAGING SYSTEM EXTENDED FIELD-OF-VIEW

FIELD OF THE INVENTION

The following generally relates to imaging, and more specifically to estimating a portion of an object or subject outside of a field-of-view, and is described with particular application to computed tomography (CT) medical imaging, but it also amenable to other imaging modalities.

BACKGROUND OF THE INVENTION

Figure 1:
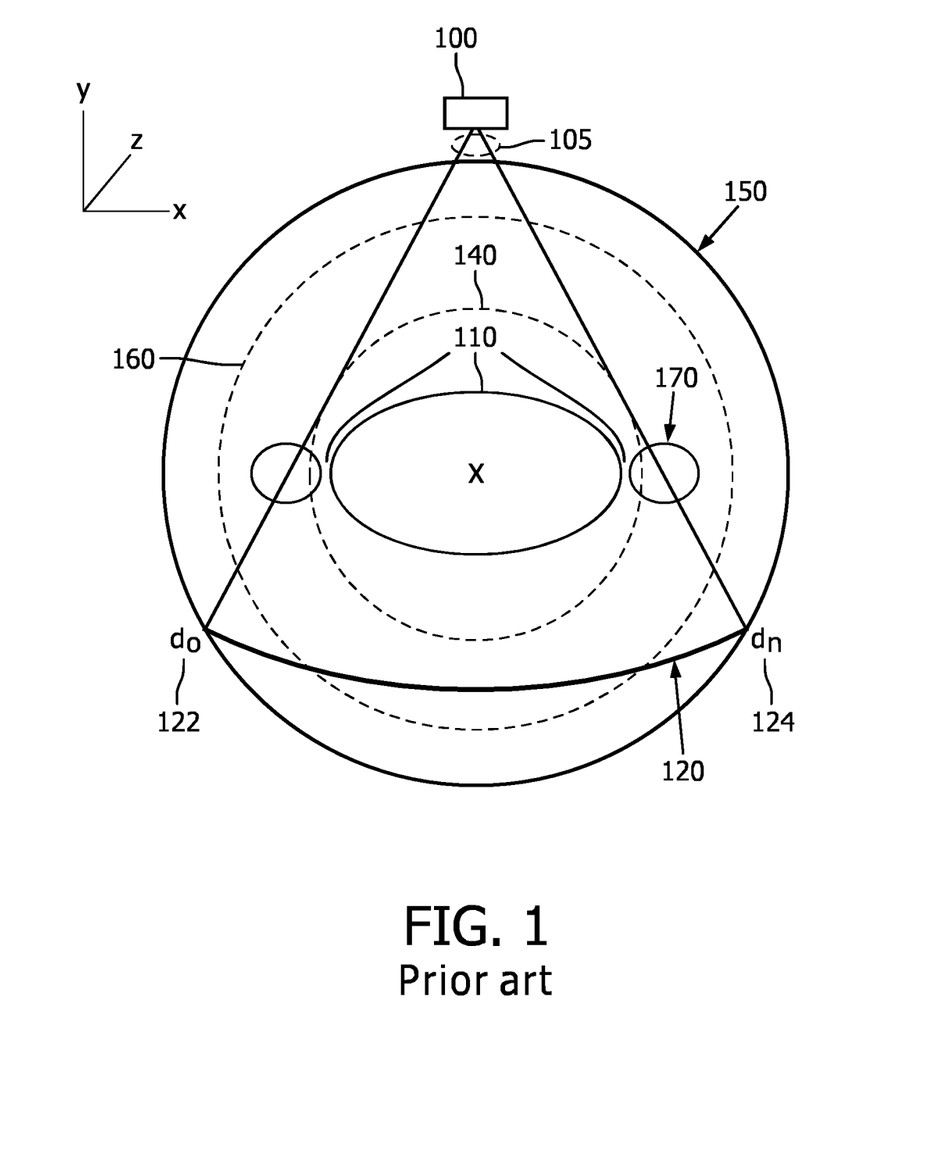
FIG. 1 schematically illustrates a prior art field-of-view.

An example CT imaging device is shown in FIG. 1. The CT imaging device includes a source 100 that emits x-ray radiation 105 that traverses a portion of a subject or object 110 and that is detected by detectors 120, $d_0$ 122, ... $d_n$ 124. For volumetric scanning, the source 100 and the detectors 120 rotate in coordination about the object 110. As they rotate, the detectors 120 detect radiation at a predetermined plurality of arcs along a rotation path (acquisition intervals). For each acquisition interval, each detector $d_i$ detects x-ray radiation impinging thereon and generates an electrical signal indicative of a total x-ray attenuation along a path from the source 100 to the detector 120 (a line integral or projection data). A set of line integrals for an acquisition interval is referred to as a projection or view.

A field-of-view (FOV) 140 is defined by the relative position of the source 100 and the detectors 120, and a length of the detectors 120, which may be constrained by a size of an aperture of an opening or bore 150. The FOV 140 can be thought of as the area within a virtual circle concentric with a center X of the bore 150 and bounded by peripheral x-rays 105 (which are tangent to the virtual circle) traversing from the source 100 to the outer detectors $d_0$ and $d_n$ as the source 100 and the detectors 120 rotate. That is, the FOV 140 includes a region of the bore 150 that is commonly traversed by the emitted radiation 105 from different rotational positions of each projection view. For a portion of a subject and/or an object 170 outside of the FOV 140, incomplete data is acquired as some data is not acquired for this region for at least 180 degrees plus a fan angle, which results in partial scan artifacts when the projection data is reconstructed into volumetric image data. Unfortunately, the partial scan artifacts may render the object 170 outside of the FOV 140 in the volumetric image data unsuitable for diagnostic or treatment planning purposes.

One approach to address truncation artifacts, as indicated by J. Hsieh et al. in "A novel reconstruction algorithm to extend the CT scan field-of-view" (2004), is to build CT imaging systems with larger bores 150 and larger FOVs 140 such that the object 110 fits entirely within the FOV 140. Another approach described by Hsieh is to fit lines to attenuation values detected for each truncated view, $k_i$, using a partial water cylinder. This approach is not accurate for all object shapes, however, and can lead to artifacts. Another approach described by S. Hsieh in "An algorithm to estimate the object support in truncated images" (2014) attempts to estimate the truncated portion of the object by an iterative approach. Unfortunately this can be time consuming and computationally expensive. The following invention provides a fast and accurate method for estimate the object extent directly in the sinogram domain.

SUMMARY OF THE INVENTION

Aspects described herein address the above-referenced problems and others.

The following describes embodiments of a system and method for estimating an extent of a subject in an extended field-of-view by fitting a curve to a sampled edge of a portion of the subject across a plurality of views in a sinogram. The sampled portion of the subject can include leading and/or trailing edges of the portion of the subject that are truncated in a set of views. The estimated extent of the subject can be inverted and backprojected to the image domain as a mask. The mask can be refined with other algorithms in the image domain. An image can be generated of the subject by using the mask in the image domain or by using the extent estimated by the fitted curve in the projection domain.

In one aspect, an imaging system includes a rotating gantry with a bore, and an X-ray radiation source supported by the rotating gantry, which rotates around the bore and emit X-ray radiation that traverses at least a portion of the bore. A detector array supported by the rotating gantry, located opposite the X-ray radiation source, detects the X-ray radiation having traversed an object located within the bore and generates projection data indicative of the detected X-ray radiation. The projection data comprises a sinogram. A processor estimates a portion of the object truncated in the sinogram by fitting a curve to data sampled from a plurality of views of the object in the sinogram adjacent to a set of truncated views of the object in the sinogram, and reconstructs an image of the object based on the estimated portion of the object truncated and the generated projection data.

In another aspect, a method for imaging includes receiving a sinogram of an object generated by a detector array. A portion of the object truncated in the sinogram is estimated by fitting a curve to data sampled from a plurality of views of the object in the sinogram adjacent to a set of truncated views of the object in the sinogram. An image of the object is reconstructed based on the estimated portion of the object truncated and the sinogram.

In another aspect, a non-transitory computer-readable storage medium carrying instructions controls one or more processors to receive a sinogram of an object generated by a detector array and estimate a portion of the object truncated in the sinogram by fitting a curve to data sampled from a plurality of views of the object in the sinogram adjacent a set of truncated views of the object in the sinogram. The one or more processors are further controlled to reconstruct an image of the object based on the estimated portion of the object truncated and the sinogram.

These and other aspects of the invention will be apparent from and elucidated with reference to the embodiment(s) described hereinafter.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 2:
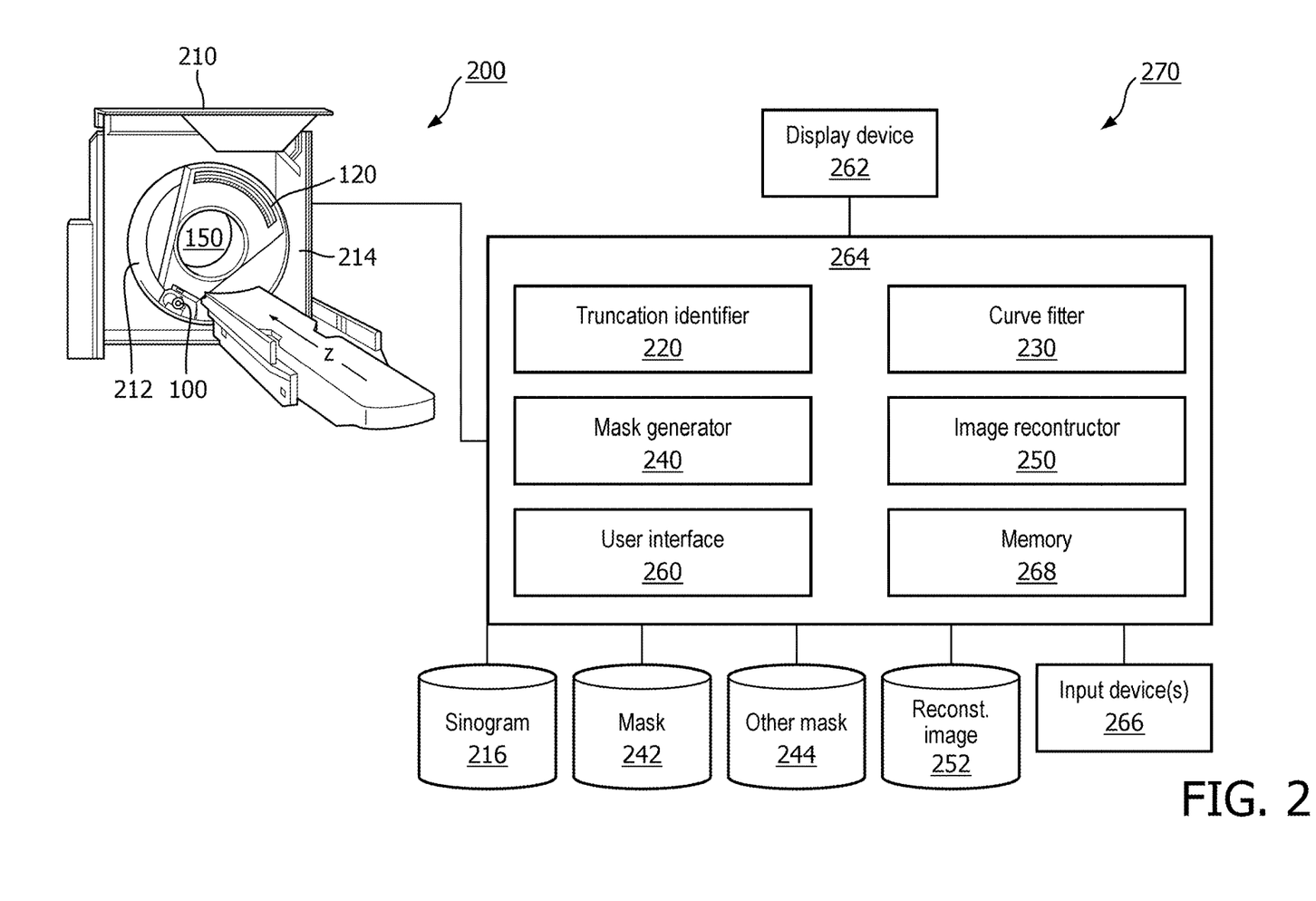
FIG. 2 illustrates an embodiment of a CT system that estimates an extent of an object or subject within an extended field-of-view.

With reference to FIG. 2, an embodiment of a system 200 that estimates an extent of the object or subject 110 outside of a field-of-view (FOV) 140 that is within an extended field-of-view (eFOV) 160 is schematically illustrated. The FOV 140 includes a region of the bore 150 that is commonly detected at each rotational position. The eFOV 160 includes a second region within the bore 150 that excludes the FOV 140 and is detected at least one rotational position.

The system 200 can include a CT imaging device 210, which includes a rotating gantry 212 supported by a stationary gantry 214. The rotating gantry supports the source 100 and the detectors 120. The detectors 120 generate projection data of the object 110, which can be stored and/or displayed as a sinogram 216. The sinogram 216 is a 2-D array of attenuation values arranged as projection/view ($k_i$) versus detector, $d_0, \ldots d_n$. The views in the sinogram 216 are ordered by rotational position, for example, consecutive rotational positions. The detectors 120 can include an M×N array of individual detectors where M and N are integers equal to or greater than one, M is along the "z" direction, and N is along a direction transverse to the "z" direction, for example, in an x-y plane. The following is described using a 1×N array of detectors 120, which is extendable to the M×N array.

Figure 3:
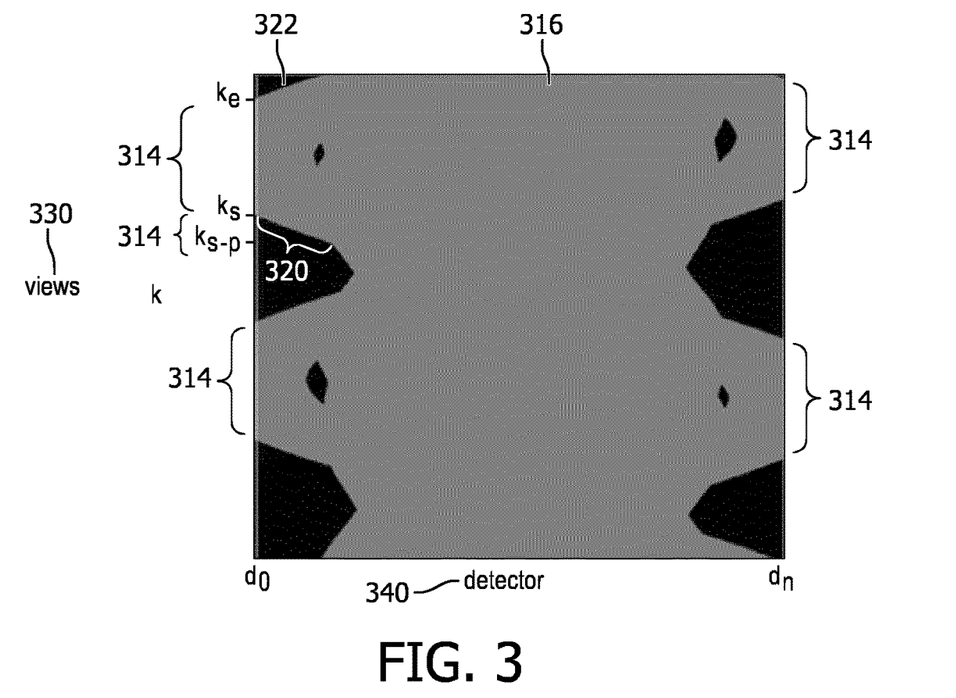
FIG. 3 illustrates an example simulated two-dimensional sinogram of an object or subject with truncation.

A truncation identifier 220 identifies a range or set of truncated views 314, $k_s$ to $k_e$. Examples of the truncated views 314 are illustrated in a simulated sinogram 316 of FIG. 3. Each set of truncated views 314 represents a group of views that include consecutive rotational positions. In FIG. 3, views 330 are represented on the vertical axis and detectors 340 are represented on the horizontal axis, and truncation is identified where a leading detector, $d_0$, changes from an attenuation value indicative of air to an attenuation value indicative of non-air, such as values indicative of skin, soft tissue, or other predetermined value, or where a trailing detector, $d_n$, changes from an attenuation value indicative of air to an attenuation value indicative of non-air. The identified truncated views 314, $k_s$ to $k_e$, correspond to a start and an end of one truncation. These truncated views 314 represent where the portion of the object or subject 170 leaves the path of the detected radiation and then re-enters the path of the detected radiation as the source 100 and detector 120 rotate.

With reference to FIGS. 2 and 3, the truncation identifier 220 identifies detectors of a leading edge 320 and/or a trailing edge 322 of the portion of the object or subject 170 across a plurality of views 330 preceding and/or following the views of the identified truncation, respectively. For example, the truncation identifier 220 identifies the leading edge 320 for the views, $k_{s-1}$ to $k_{s-p}$, where p is a predetermined integer number of views, and the initial detector, $d_0$, of the detectors 120 is in the direction of rotation. The value of p can be a predetermined value, a statistical sampling criteria, combinations thereof, and/or other value. The detector in each view of the views 330 of the leading edge 320 includes a first detector $d_j$, where the attenuation value from the first detector $d_j$ to a next detector $d_{j-1}$ in a same view changes from air (or other predetermined value) to the portion of the object or subject 170. The trailing edge 322 is similarly identified. The leading edge 320 and/or trailing edge 322 correspond to outer detectors in the detector array 120, such as first detectors, $(d_0, \ldots d_p)$, in the direction of rotation and/or last detectors, $(d_{n-p}, \ldots, d_n)$, following the direction of rotation.

Figure 4:
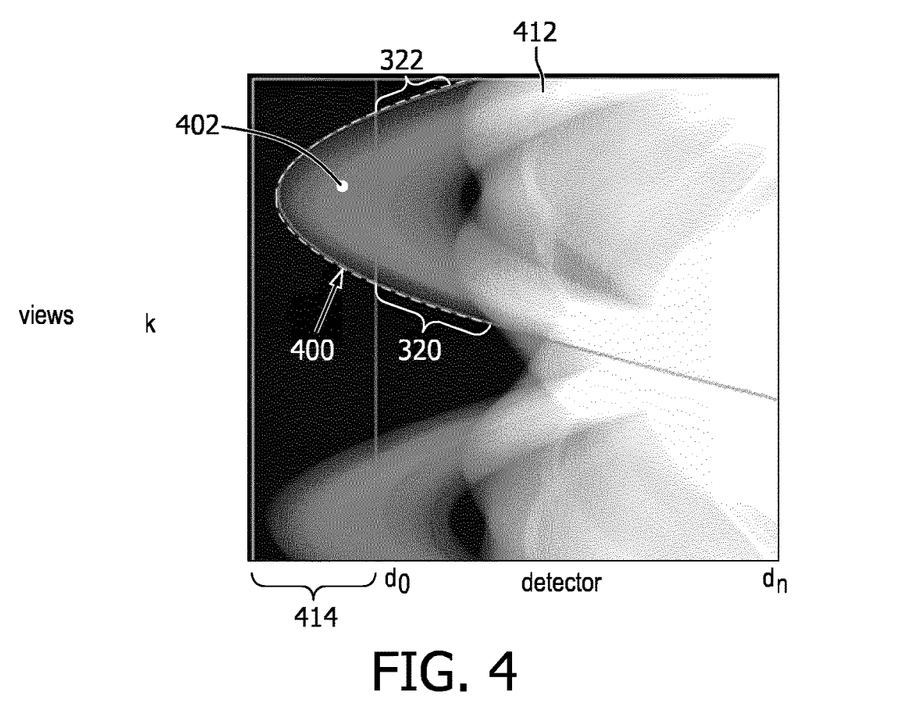
FIG. 4 illustrates an example portion of a simulated two-dimensional sinogram of an object and/or subject with virtual data used to augment truncated data to provide complete data within an extended field-of-view.

With reference to FIGS. 2-4, a curve fitter 230 fits a curve 400 to the identified views as a function of the identified detector position of the leading edge 320 of the object 110, the trailing edge 322 of the object 110, or combinations thereof. In FIG. 4, the fitted curve 400 is illustrated in a partial simulated sinogram 412 with virtual detectors 414. The fitted curve 400 defines an extent 402 of the portion of the object or subject 170 in the extended field-of-view 160 using the virtual detectors 414. That is, the extent 402 includes an area between the fitted line 400 and a line of an initial detector at an edge of the truncated views 314, such as $d_0$ or $d_n$. The fitted curve 400 is fitted based on a sample set that includes sampled detector positions of the leading edge 320 and/or the trailing edge 322 in the sinogram 120. Such a line is fitted for each identified set of truncated views 314 of the object or subject 170.

With reference to FIGS. 2-5, a mask generator 240 can generate an image mask 242 (FIG. 5), propagated from the sinogram 216 with the extents in the extended field-of-view defined by the fitted lines 400 and backprojected to the image domain. The image mask 242, such as a binary image mask (e.g., black and one other value), includes a first value 500 indicative of the object 110 and a second value 510 indicative of air or non-subject. The first values 500 and second values 510 are represented in an x-y coordinate system of the image domain. The image mask 242 can be used to refine other image domain masks 244 using current methods of image reconstruction. For example, the image mask 242 can be refined using an intersection of the image mask 242 and the other image domain mask 244. The image mask 242 can be filled with attenuation values, such as water or other predetermined value.

With continuing reference to FIGS. 2-5, an image reconstructor 250 reconstructs an image 252 of the object 110 based on the extent 402 of the object 110 defined by the fitted line 400 and the sinogram 216. In one embodiment(s), the image reconstructor 250 uses the extent 402 as an additional constraint to further improve a data extrapolation technique in the projection domain. For example, lines from fitting the partial water cylinder to the individual views can be smoothed using the fitted line 400.

Figure 5:
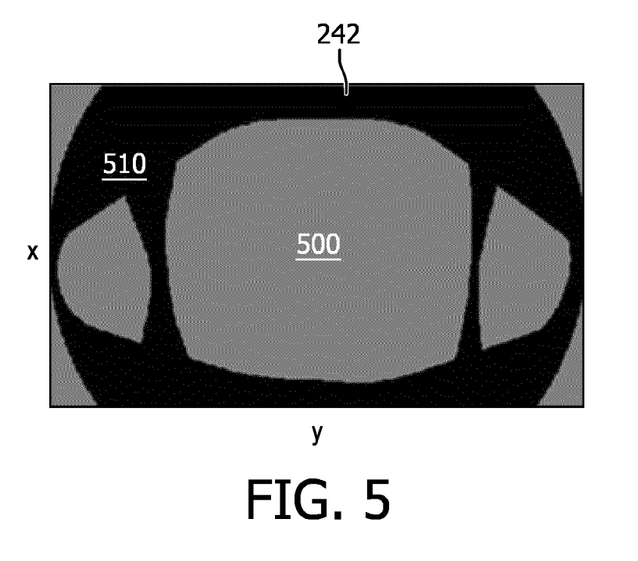
FIG. 5 illustrates an example image mask in the image domain propagated from extents estimated by a fitted curve in the projection domain.

In some embodiments, the image reconstructor 250 uses the image mask 242 or refinements thereof in a reconstruction or an iterative reconstruction. For example, the portion of the subject 170 in the extended field-of-view defined by the image mask 242 in the reconstructed image 252 can be filled with an estimated Hounsfield Unit (HU), such as indicative of water or other material. In some instances, the filled portion in the eFOV 160 provides a computationally fast estimate of sufficient quality for some radiotherapy applications. A refinement smooths the transition by radially extrapolating the image details within the FOV 140 and then blends the result with the reconstructed image filled in the eFOV 160 using the estimated HU.

A further refinement can add additional details to the eFOV 160 in the refined image by forward projecting the refined image into the projection domain, and using a portion of the forward projection in the eFOV 160 represented with the virtual detectors 414 and the sinogram 216 to create a refined sinogram with estimated portion of the object 110 or extents 402 using the virtual detectors 414. The refined sinogram with extents 402 can then be backprojected to generate the reconstructed image 252. In some instances, the further refinement can provide additional details of the object in the eFOV 160.

With continuing reference to FIGS. 2-5, a user interface 260 can display the reconstructed image 252 on a display device 262 and/or store the image 252 in a storage subsystem, such as a Picture Archiving and Communication System (PACS), Radiology Information System (RIS), Electronic Medical Record (EMR) and the like.

The truncation identifier 220, the curve fitter 230, the mask generator 240, the image reconstructor 250, and the user interface 260 are suitably embodied by a configured computer processor 264, such as a digital processor, a microprocessor, an electronic processor, an optical processor, a multi-processor, a distribution of processors including peer-to-peer or cooperatively operating processors, client-server arrangement of processors, and the like and configured to identify truncated views, identify and sample leading edges 320 and/or trailing edges 322, fit the curve 400, generate the image mask 242, reconstruct the image 252, and operate the display device 262 and one or more input devices 266.

The configured computer processor executes at least one computer readable instruction stored in the computer readable storage medium 268, such as an optical disk, a magnetic disk, semiconductor memory of a computing device with the configured processor, which excludes transitory medium and includes physical memory and/or other non-transitory medium to perform the disclosed techniques. The configured processor may also execute one or more computer readable instructions carried by a carrier wave, a signal or other transitory medium. The lines between components in represented in the diagram of FIG. 2 represent communications paths.

The configured processor 264, the display device 262, and the input device(s) 266 can comprise a computing device 270, such as a console, a laptop computer, desktop computer, tablet computer, smartphone, body worn computing device, server, distributed or cooperative arrangement of computing devices, and the like. The display device 262 is suitably embodied by a computer display, smartphone display, projector, body worn display, television (TV), combinations thereof, and the like. The input device 266 is suitably embodied by a keyboard, a mouse, a trackball, a microphone, combinations thereof, and the like.

The sinogram 216, the image mask 242, the other image domain mask 244, and the reconstructed image 252 are suitably embodied by an electronic or computer memory, which can include data structures, file structures, database organization, image formats, and the like.

In some embodiments, the truncation identifier 220, the curve fitter 230, the mask generator 240, the image reconstructor 250, and the user interface 260 are suitably embodied as computer program products.

Figure 6:
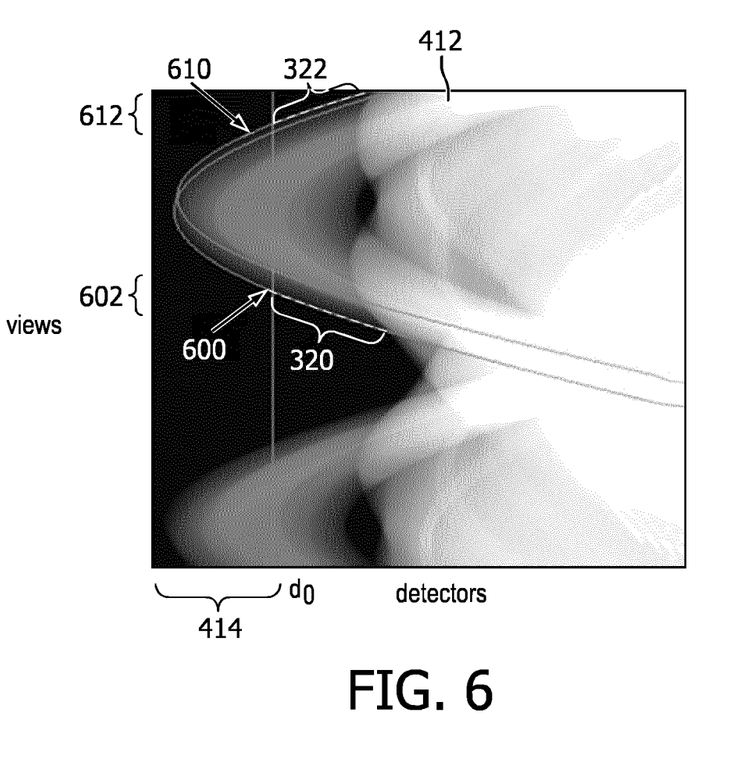
FIG. 6 illustrates an example curve fitting to sampled edges of a portion of the object or subject across a plurality of views in a sinogram.

With reference to FIG. 6, an example curve fitting to sampled edges 320, 322 of a portion of the object 110 across a plurality of views in the simulated sinogram 412 is diagrammatically illustrated. In FIG. 6, a first sinusoid curve 600 is fitted to the leading edge 320 across a first sampled plurality of views 602. A second sinusoid curve 610 is fitted to the trailing edge 322 across a second sampled plurality of views 612. The sample sets can be represented as $(\hat{k}, \hat{d})$ where $\hat{d}=f(\hat{k})$, where $\hat{k}$ is a view identifier and $\hat{d}$ is a detector identifier or position.

A sinusoid function can include:

$$f_{a,b,c}(k) = a*\sin\left(b*k*\frac{2\pi}{N}+c\right)+s,$$

where a represents an amplitude, b represents a frequency, k is the view, c represents a phase, N is the number of views per revolution, and s is an offset from the center of rotation. An objective function is defined for a mean squared error between the fitted sinusoid and sample sets as $\varphi_{a,b,c}=\Sigma_k(f_{a,b,c}(k)-f(\hat{k}))^2$. Values for a, b, c which minimize the objective function can be found using a numerical methods algorithm, such as the Nelder-Mead simplex algorithm or other numerical method or other algorithm.

The first sinusoid curve 600 and the second sinusoid curve 610 can be interpolated to produce the fitted curve 400. For example, the fitted curve 400 can be interpolated pointwise using an average, weighted average or other function of the first sinusoid curve 600 and the second sinusoid curve 610. One mathematical expression for an interpolation between two curves defined by two sets of parameters (a1,b1,c1) and (a2,b2,c2), is given by $$f(k) = \left(\frac{k}{nk}\right) \cdot f_{a1,b1,c1}(k) + \frac{nk-k}{nk} \cdot f_{a12,b2,c2}(k),$$

where nk expresses the number of truncated views from $k_s$ to $k_e$.

Figure 7:
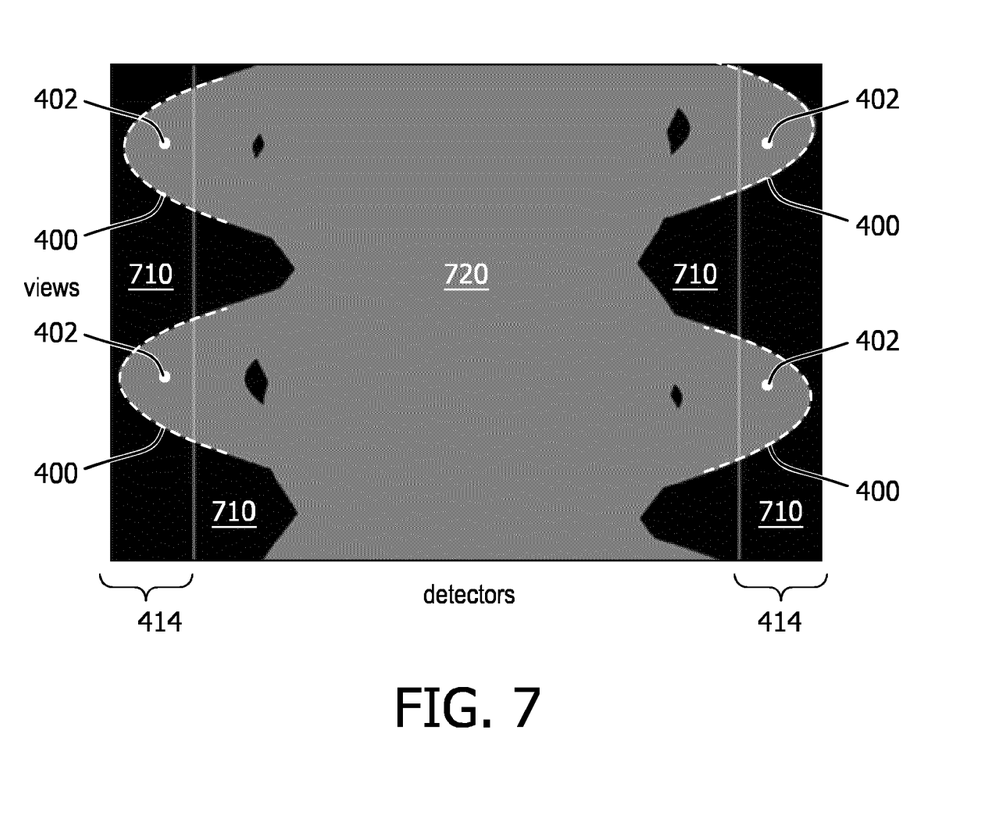
FIG. 7 illustrates an example projection domain mask including estimated extents.

With reference to FIG. 7, an example projection domain mask or sinogram mask 700 with extents 402 is illustrated. The sinogram mask 700 illustrates the extents in the eFOV 160 using the virtual detectors 414. The sinogram mask 700 includes a first region 710 of detected x-rays that do not contribute to the image and pass only through air. The sinogram mask 700 includes a second region 720 of detected x-rays that contribute to the image and pass through some part of the object 110.

The sinogram mask 700 with extents 402 can be inverted and backprojected to image domain. The resulting mask image identifies areas where rays that pass-through air contribute to the image and all other areas that do not contribute to the image. A second inversion yields the image mask 242 that indicates the area of the object 110 in the image domain, such as illustrated in FIG. 5.

Figure 8:
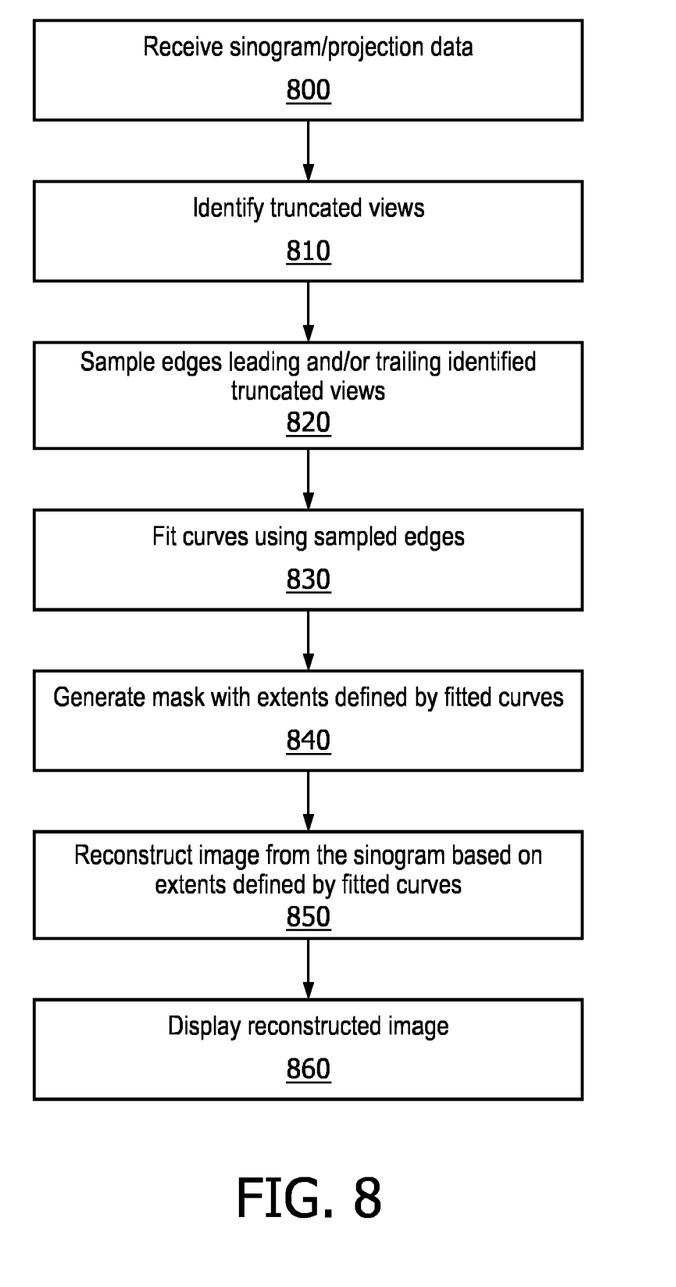
FIG. 8 illustrates a flowchart in accordance with an embodiment(s) herein.

FIG. 8 illustrates a flowchart in accordance with an embodiment(s) herein.

At 800, a sinogram 216 of the subject is received. The sinogram 216 can be received directly from and generated by the CT imaging device 210, or received indirectly from a storage subsystem. The sinogram 216 comprises projection data. For example, each row represents a view of the object 110 from an ordered rotational position and each column represents a detector of a detector array ordered spatially.

At 810, sets of truncated views 314 are identified in the received sinogram 216. The sets of truncated views 314 can be identified by a leading or a trailing detectors having attenuation values above a predetermined threshold, such as values above that of air.

At 820, for each set of truncated views 314, edges of the object 110 represented in the sinogram 216 are sampled across a plurality of views. The sampled edges include detector positions and view identifiers of the leading edges 320 and/or trailing edges 322 of the object 110. The leading edge 320 immediately follows the set of truncated views 314. The trailing edge 322 immediately precedes the set of truncated views 314.

At 830, for each set of truncated views 314, the curve 400 is fit to the sampled edges. The fitted curve 400 includes a detector position or location, extended to virtual detectors 414, as a function of the view. The fitted curve 400 can comprise an interpolation of two fitted curves 600, 610, a first curve 600 fitted to the sampled leading edge 320, and a second curve 610 fitted to the sampled trailing edge 322. Other fitted curves are contemplated.

At 840, the sinogram mask 700 is generated and propagated to the image domain with the extents 402 defined by the fitted curves 400 for each set of truncated views 314 as the image mask 242. The image mask 242 can be refined using other image domain masks 244, which define the spatial area or volume occupied by the object 110 within the field-of-view 140 and extended field-of-view 160. In some embodiments, the image mask 242 can be omitted and the extents 402 defined by the fitted curves 400 in the projection domain used to further refine other techniques that define the extents 402 within the projection domain.

At 850, the image 252 of the object 110 can be reconstructed from the sinogram 212 based on the extents 402 defined by the fitted curves 400. The image 252 can be reconstructed using the image mask 242 in the image domain and the sinogram 252. The image 252 can be reconstructed using projection data defined by or refined with the extents 402 defined by the fitted curves 400.

At 860, the reconstructed image 252 can be displayed on the display device 262 and/or stored in a storage subsystem.

The above may be implemented by way of computer readable instructions, encoded or embedded on a computer readable storage medium, which, when executed by a computer processor(s), cause the processor(s) to carry out the described acts. Additionally or alternatively, at least one of the computer readable instructions is carried out by a signal, carrier wave or other transitory medium.

The above steps can be performed in a different order and/or some steps can be omitted.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with, or as part of other hardware, but may also be distributed in other forms, such as via the Internet or other wired or wireless telecommunication systems. Any reference signs in the claims should not be construed as limiting the scope.

The invention claimed is:

1. An imaging system, comprising:
a rotating gantry with a bore;
an X-ray radiation source supported by the rotating gantry, and configured to rotate around the bore and emit X-ray radiation that traverses at least a portion of the bore;
a detector array supported by the rotating gantry, located opposite the X-ray radiation source, and configured to detect the X-ray radiation having traversed an object located within the bore and generate projection data indicative of the detected X-ray radiation, wherein the projection data comprises a sinogram; and
at least one processor configured to:
estimate a portion of the object truncated in the sinogram by:
determining a plurality of views as comprising at least one sampled edge, wherein the at least one sampled edge comprises a leading edge of the object and a trailing edge of the object adjacent a set of truncated views, wherein the leading edge and the trailing edge comprise detector positions and view identifiers;
fitting a first sinusoid curve to the leading edge of the object;
fitting a second sinusoid curve to the trailing edge of the object; and
interpolating between the first sinusoid curve and the second sinusoid curve, to fit a curve to the leading edge and the trailing edge; and
reconstruct an image of the object based on the estimated portion of the object truncated and the generated projection data.

2. The system according to claim 1, wherein the at least one processor is further configured to:
estimate each extent of the object in each set of truncated views located outside a field-of-view and in an extended field-of-view according to each fitted curve, wherein a region within the bore commonly detected at each rotational position defines a field-of-view, wherein a second region of the bore excluding the field-of-view detected at at least one rotational position defines an extended field-of-view, wherein the generated projection data at each rotational position defines a view.

3. The system according to claim 1, wherein the at least one processor is further configured to:
detect the set of truncated views of the object, wherein the at least one sampled edge comprises a set of views adjacent the set of truncated views of the object.

4. The system according to claim 1, wherein the fitted curve includes a detector position as a function of the view, and wherein the detector positions of the fitted curve includes positions of virtual detectors.

5. The system according to claim 1, wherein the at least one processor is further configured to:
generate an image mask within a coordinate system of an image domain based on the estimated portion of the object truncated in the sinogram according to the fitted curve, wherein the image mask represents an area or a volume of the object within a field-of-view and an extended field-of-view in the image domain.

6. A method for imaging, comprising:
receiving a sinogram of an object generated by a detector array;
estimating a portion of the object truncated in the sinogram by:
   determining a plurality of views as comprising at least one sampled edge, wherein the at least one sampled edge comprises a leading edge of the object and a trailing edge of the object adjacent a set of truncated views wherein the leading edge and the trailing edge comprise detector positions and view identifiers;
   fitting a first sinusoid curve to the leading edge of the object;
   fitting a second sinusoid curve to the trailing edge of the object; and
   interpolating between the first sinusoid curve and the second sinusoid curve, to fit a curve to the leading edge and the trailing edge; and
reconstructing an image of the object based on the estimated portion of the object truncated and the sinogram.

7. The method according to claim 6, wherein estimating the curve comprises:
estimating each extent of the object in each set of truncated views located outside a field-of-view and in an extended field-of-view according to each fitted curve, wherein a region within a bore of a imaging device commonly detected at each rotational position of the detector array and a source around the bore defines a field-of-view, wherein a second region of the bore excluding the field-of-view detected at at least one rotational position defines an extended field-of-view, wherein generated projection data at each rotational position defines a view.

8. The method according to claim 6, further comprising:
detecting the set of truncated views of the object, wherein the at least one sampled edge comprises a set of views adjacent the set of truncated views of the object.

9. The method according to claim 6, wherein the fitted curve is a detector position as a function of the view, wherein the detector positions of the fitted curve includes positions of virtual detectors.

10. The method according to claim 6, further comprising:
generating an image mask within a coordinate system of an image domain based on the estimated portion of the object truncated in the sinogram according to the fitted curve, wherein the mask represents an area or a volume of the object within a field-of-view and an extended field-of-view in the image domain.

11. A non-transitory computer-readable storage medium having one or more executable instructions stored thereon which, when executed by at least one processor, cause the at least one processor to perform an imaging method, the imaging method comprising:
receiving a sinogram of an object generated by a detector array;
estimating a portion of the object truncated in the sinogram by:
   determining a plurality of views as comprising at least one sampled edge, wherein the at least one sampled edge comprises a leading edge of the object and a trailing edge of the object adjacent a set of truncated views, wherein the leading edge and the trailing edge comprise detector positions and view identifiers;
   fitting a first sinusoid curve to the leading edge of the object;
   fitting a second sinusoid curve to the trailing edge of the object; and
   interpolating between the first sinusoid curve and the second sinusoid curve, to fit a curve to the leading edge and the trailing edge; and
reconstructing an image of the object based on the estimated portion of the object truncated and the sinogram.

12. The non-transitory computer-readable storage medium according to claim 11, the imaging method further comprising:
generating an image mask within a coordinate system of an image domain based on the estimated portion of the object truncated in the sinogram according to the fitted curve, wherein the image mask represents an area or a volume of the object within a field-of-view and an extended field-of-view in the image domain.

13. The non-transitory computer-readable storage medium according to claim 11, the imaging method further comprising:
estimating each extent of the object in each set of truncated views located outside a field-of-view and in an extended field-of-view according to each fitted curve, wherein a region within a bore of a imaging device commonly detected at each rotational position of the detector array and a source around the bore defines a field-of-view, wherein a second region of the bore excluding the field-of-view detected at at least one rotational position defines an extended field-of-view, wherein generated projection data at each rotational position defines a view.

14. The non-transitory computer-readable storage medium according to claim 11, the imaging method further comprising:
detecting the set of truncated views of the object, wherein the at least one sampled edge comprises a set of views adjacent the set of truncated views of the object.

* * * * *